US012414722B2

(12) United States Patent
Baumer et al.

(10) Patent No.: US 12,414,722 B2
(45) Date of Patent: Sep. 16, 2025

(54) PORTABLE CARDIAC MONITORING DEVICE AND ASSOCIATED CARDIAC MONITORING SYSTEM AND NETWORK

(71) Applicant: Inovise Medical, Inc., Beaverton, OR (US)

(72) Inventors: Martin Baumer, Carlton, OR (US); Alan V. Andresen, Portland, OR (US)

(73) Assignee: Inovise Medical, Inc., Beaverton, OR (US)

( * ) Notice: Subject to any disclaimer, the term of this patent is extended or adjusted under 35 U.S.C. 154(b) by 407 days.

(21) Appl. No.: 18/082,500

(22) Filed: Dec. 15, 2022

(65) Prior Publication Data

US 2023/0200708 A1 Jun. 29, 2023

Related U.S. Application Data

(60) Provisional application No. 63/294,364, filed on Dec. 28, 2021.

(51) Int. Cl.
*A61B 5/332* (2021.01)
*A61B 5/00* (2006.01)
(Continued)

(52) U.S. Cl.
CPC ............ *A61B 5/332* (2021.01); *A61B 5/0006* (2013.01); *A61B 5/002* (2013.01); *A61B 5/26* (2021.01);
(Continued)

(58) Field of Classification Search
None
See application file for complete search history.

(56) References Cited

U.S. PATENT DOCUMENTS 6,491,647 B1 12/2002 Bridger et al.
7,010,342 B2 3/2006 Galen et al.
(Continued)

OTHER PUBLICATIONS

COALA; https://www.coalalife.com/us/; Accessed Mar. 7, 2023.
(Continued)

*Primary Examiner* — Ankit D Tejani
(74) *Attorney, Agent, or Firm* — LOZA & LOZA, LLP; David S. Sarisky

(57) ABSTRACT

A device includes a main body having a length, a first end, a second end, and an axis along the length. A first electrode is associated with the first end of the main body. A suspension structure is associated with the second end of the main body. The suspension structure is configured for displacement in a direction of the axis of the main body, and includes a flexible isolation ring defining an opening, and a second electrode that is associated with the opening and mechanically coupled to the flexible isolation ring. The device also includes an electronics assembly with a first subassembly that is electrically coupled to the first electrode and secured relative to the main body to prevent displacement of the first subassembly in a direction of the axis of the main body, a second subassembly that is arranged to electrically couple with the second electrode. A flexible coupling between the first subassembly and the second subassembly enables displacement of the second subassembly relative to the first subassembly and in a direction of the axis of the main body.

13 Claims, 13 Drawing Sheets

(51) Int. Cl.
*A61B 5/26* (2021.01)
*A61B 5/282* (2021.01)

(52) U.S. Cl.
CPC ............ *A61B 5/282* (2021.01); *A61B 5/6823* (2013.01); *A61B 5/6825* (2013.01); *A61B 5/7221* (2013.01); *A61B 2560/0214* (2013.01); *A61B 2560/0456* (2013.01); *A61B 2562/0209* (2013.01); *A61B 2562/166* (2013.01); *A61B 2562/227* (2013.01)

(56) References Cited

U.S. PATENT DOCUMENTS

| | | |
|---|---|---|
| 7,110,804 B2 | 9/2006 | Baumer et al. |
| 9,451,896 B2 | 9/2016 | Bauer |
| 2016/0174894 A1 | 6/2016 | Proud |
| 2017/0136178 A1 | 5/2017 | Kamen et al. |
| 2021/0345939 A1* | 11/2021 | Jumbe .................... H04R 1/028 |
| 2021/0358472 A1* | 11/2021 | Chang .................. G10K 11/341 |

OTHER PUBLICATIONS

EkoHealth; https://www.ekohealth.com/; Accessed Mar. 7, 2023.
AUM Cardiovascular; https://www.imedicalapps.com/2017/08/aum-cardiovasculars-cadence-device-fda/; Accessed Mar. 7, 2023.
International Search Report, International Patent Application No. PCT/US2022/053081, May 9, 2023, 6 pgs.
Written Opinion, International Patent Application No. PCT/US2022/053081, May 9, 2023, 12 pgs.
Partial International Search Report, International Patent Application No. PCT/US2022/053081, Mar. 15, 2023, 11 pgs.
International Preliminary Report on Patentability, International Patent Application No. PCT/US2022/053081, Dec. 12, 2023, 9 pgs.

* cited by examiner

PORTABLE CARDIAC MONITORING DEVICE AND ASSOCIATED CARDIAC MONITORING SYSTEM AND NETWORK

CROSS-REFERENCE TO RELATED APPLICATION

This application claims the benefit of U.S. Provisional Application Ser. No. 63/294,364, entitled "Portable Cardiac Monitoring Device and Associated Cardiac Monitoring System and Network" and filed on Dec. 28, 2021, which is expressly incorporated by reference herein in its entirety.

TECHNICAL FIELD

The present disclosure relates generally to devices, systems, and networks for monitoring cardiac function, and more particularly, to a portable, handheld device for cardiac monitoring by a user outside a clinical setting and in association with a monitoring system and network.

BACKGROUND

One of the greatest current challenges for medical systems worldwide is managing the growing number of patients with heart diseases. Regarding this important concern, the U.S. alone has millions of people with heart failure, and currently, over a half million new heart-failure patients are diagnosed each year. Heart failure is only one form of heart disease, but one of the most expensive ones for health care systems. The heart-failure challenge is growing globally with another sixty million, or so, patients outside of the U.S. About 50% of these other patients are in Asia, and the number in many developing countries is unknown due to the lack of diagnostic means and public information. Heart failure is a disease of the elderly, and it is growing rapidly in all societies with aging populations, and it is an epidemic burden for the health care system in every country.

Key issues with the management of heart diseases arise both from the lack of simple, inexpensive, non-invasive ways to diagnose, evaluate, and monitor treatment for cardiac patients, and from the growing need to evaluate and monitor such patients as much as possible outside a clinical setting, e.g., hospital, physician's office, etc.

Both acoustic cardiography and non-acoustic cardiography are low cost, non-invasive diagnostic technologies that enable fast assessment of a patient's cardiac function. These technologies provide nearly as much insight into heart function as ultrasound technology. A typical cardiography test is most often performed in the realm of acoustic cardiography and involves simultaneous acquisition of both electrocardiogram (ECG) data and heart-sound data, and analysis thereof. Non-acoustic cardiography involves acquisition and analysis of only ECG data.

Known equipment employed for cardiography testing rely on relatively involved equipment models that require specific placements of electrodes on a patient's torso, and multi-wire connections to a data acquisition system. An example of such equipment used for non-acoustic cardiography is a Holter monitor, which uses electrodes attached to a patient's torso and a bulky recording device secured to the patient's waist to track cardiac activity for 24 to 72 hours.

Other known equipment employed for cardiography testing are more portable in nature and do not require wired connections to a bulky recording device. An example of such equipment is the COALA™ Heart Monitoring System (www.coalalife.com). This system includes a handheld structure having three closely spaced electrodes that are held against the chest to sense ECG activity through narrow-field sensing vectors formed at the chest. An additional far field ECG recording is captured via electrode contact of fingertips from left and right hands. The handheld structure also includes a transducer for sensing heart sounds. Another example of portable cardiography testing equipment is the Eco DUO™ (www.ekohealth.com). This system includes a handheld structure having a two closely spaced electrodes that are held against the chest to sense ECG activity through a narrow-field sensing vector. The handheld structure also includes a transducer for sensing heart sounds. The ECG sensing vectors enabled by these portable devices do not span the long axis of the heart, thereby limiting effective capture of electrical depolarization of the atria of the heart, e.g., p-waves. Accordingly, subsequent atrial fibrillation analysis by these devices will have diminished accuracy due to their inability to effectively correlate p-wave information.

Another example of portable cardiography testing equipment that enables both acoustic cardiography and non-acoustic cardiography is disclosed in U.S. Pat. No. 9,451,896, which is hereby incorporated by reference. The portable device described in the '896 patent is in a form which accommodates both acoustic and non-acoustic cardiography by a patient outside of a clinical setting. The disclosed forms include a stylus-like configuration that resembles a pen or a pencil, and a finger-mountable ring configuration which is mountable on the outer end of a subject's finger. While this portable device enables ECG sensing through a far-field vector defined by a finger electrode and a chest electrode, each of these electrodes has a small service area and thus may not provide a quality ECG signal. Furthermore, the small electrodes and stylus configuration may be difficult for a user to hold in a stable manner for a duration of time needed to capture quality ECG signals and heart sound signals.

It is therefore desirable to provide a portable cardiography device that provides a longer, far-field ECG vector that produces an ECG signal with less noise, and one in which the p-wave is more visible. The concepts disclosed below address these needs and others.

SUMMARY

In one aspect, the disclosure relates to a portable monitoring device that includes a main body having a length, a first end, a second end, and an axis along the length. A first electrode is associated with the first end of the main body. A suspension structure is associated with the second end of the main body. The suspension structure is configured for displacement in a direction of the axis of the main body, and includes a flexible isolation ring defining an opening, and a second electrode that is associated with the opening and mechanically coupled to the flexible isolation ring. As used herein "displacement in a direction of the axis" may be expressed alternatively as movement up or down relative to the axis, or movement up or down along the axis. The device also includes an electronics assembly with a first subassembly that is electrically coupled to the first electrode and secured relative to the main body to prevent displacement of the first subassembly in a direction of the axis of the main body, a second subassembly that is arranged to electrically couple with the second electrode. A flexible coupling between the first subassembly and the second subassembly enables displacement of the second subassembly relative to the first subassembly and in a direction of the axis of the main body.

In another aspect, the disclosure relates to a cardiac monitoring system that includes a portable monitoring device and dock-top case. The portable device has a main body with a charge-receiving coil. The dock-top case includes a cavity and a charge-transmitting coil that surrounding the cavity. The cavity is configured to receive a docking portion of the main body of the portable device such that the charge-receiving coil of the portable device aligns with the charge-transmitting coil of the case.

In another aspect, the disclosure relates to a cardiac monitoring network that includes a portable monitoring device, a user device, and a network server. The portable device has a first electrode shaped to be placed in abutting contact with a palm of a user hand, and a second electrode shaped to be placed in abutting contact with a chest of the user while the first electrode in abutting contact with a palm of a user hand. The portable device also includes circuitry coupled to the first electrode and the second electrode that is configured to sense electrocardiogram (ECG) activity and communication circuitry configured to transmit a signal of the sensed ECG activity. The user device has communication circuitry configured to receive the signal of the sensed ECG activity from the portable device. The network server has a communication interface configured to communicate with the user device to receive the signal of the sensed ECG activity from the user device.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein.

DETAILED DESCRIPTION

Disclosed herein is a portable, handheld device that enables one or both of acoustic cardiography and non-acoustic cardiography using a single hand. The entirety of the device forms a bulb-like structure having a dome electrode at one end and a generally planar electrode at the opposite end. A grip ring, main housing, and flexible isolation ring extend between the dome electrode and the planar electrode. An interior space formed by the dome electrode, grip ring, and main housing houses electronics subassemblies that are coupled to electrodes for purposes of sensing electrical activity of the heart, and in some embodiments to an acoustic sensor for purposes of sensing acoustic activity of the heart. The electronics subassemblies may further include a processor for analyzing sensed electrical activity of the heart (referred to herein going forward as "ECG activity"), and if so configured, acoustic activity of the heart (referred to herein going forward as "heart-sound activity") for diagnostic purposes. The electronics subassemblies may further include components that enable wireless communication with other devices. For example, the portable, handheld device may interface with a user device, e.g., a phone or other mobile device, which in turn interfaces with a network server/processor. Activity sensed by the portable device may be transmitted to the user device and provided to the network server/processor for analysis of and reporting on cardiac function.

Due to the typical advanced age of the users of this device, the device has been designed to accommodate individuals with limited motor and dexterity due to physical limitations related to joint or neurological issues that affect controlled movements of the fingers and hands. To this end, the portable device disclosed herein is designed to accommodate various levels of hand dexterity limitations by providing a shape that can be easily held and manipulated with the large muscle groups rather than relying on small muscle group control and strength. The geometry of the portable device does not require the user to hold and rotate the device in a specific orientation.

Figure 9A:
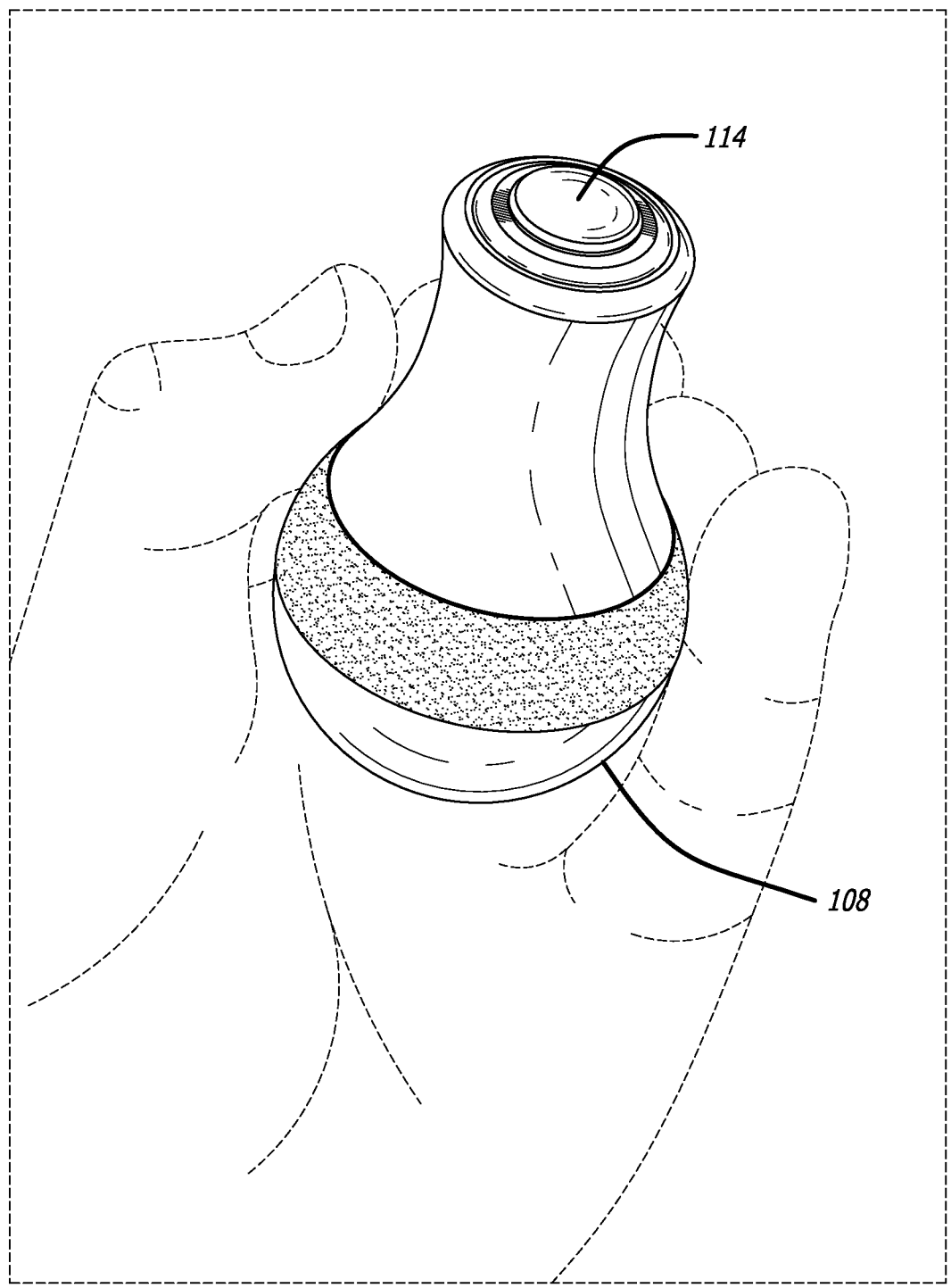
FIGS. 9A and 9B are illustration of a portable device in use.
Figure 9B:
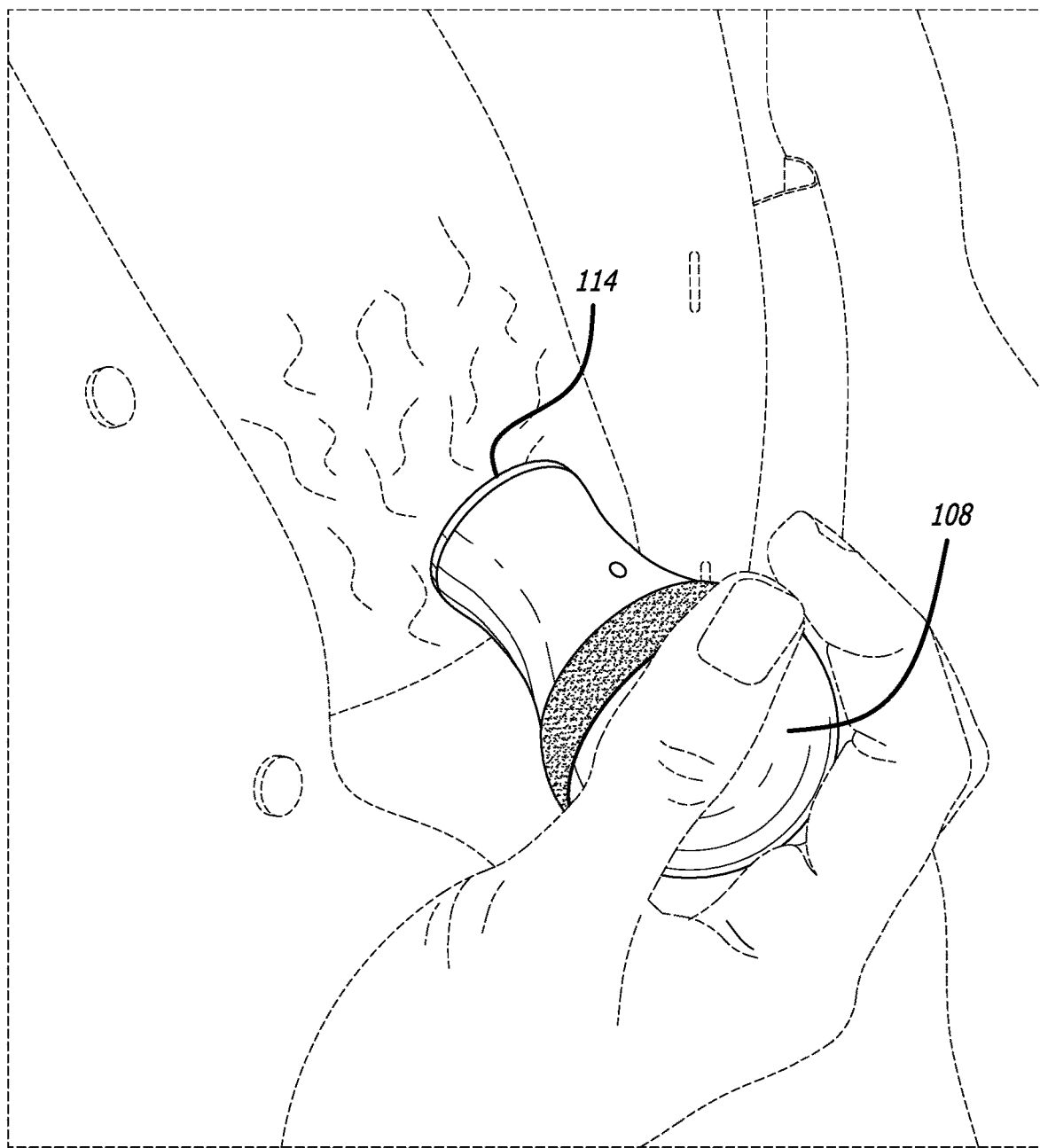

With reference to FIGS. 9A and 9B, the shape of the portable device is designed to fit inside the natural relaxed state of the hand. The size is such that the portable device comfortably fits into as small as the five percentile and as large as the 95 percentile of hand sizes. The large dome of the portable device provides an electrode that is sized to create maximum surface contact of the palm of the hand, e.g., the right hand. The large contact surface of the dome electrode also allows for flexibility in the positioning of the portable device in the hand. The tapered transition and symmetry of the housing of the portable device allows the fingers to natural drape and contact the housing for ease of control and manipulation, and to comfortably rest on the unit to add additional stability. A rubberized grip of the portable device allows users to hold the device securely without slipping.

Having generally described the geometry of the portable device and some of the benefits provided by the geometry, a more detailed description of the portable device within the contexts of a cardiac monitoring system and a cardiac monitoring network follow.

Figure 1A:
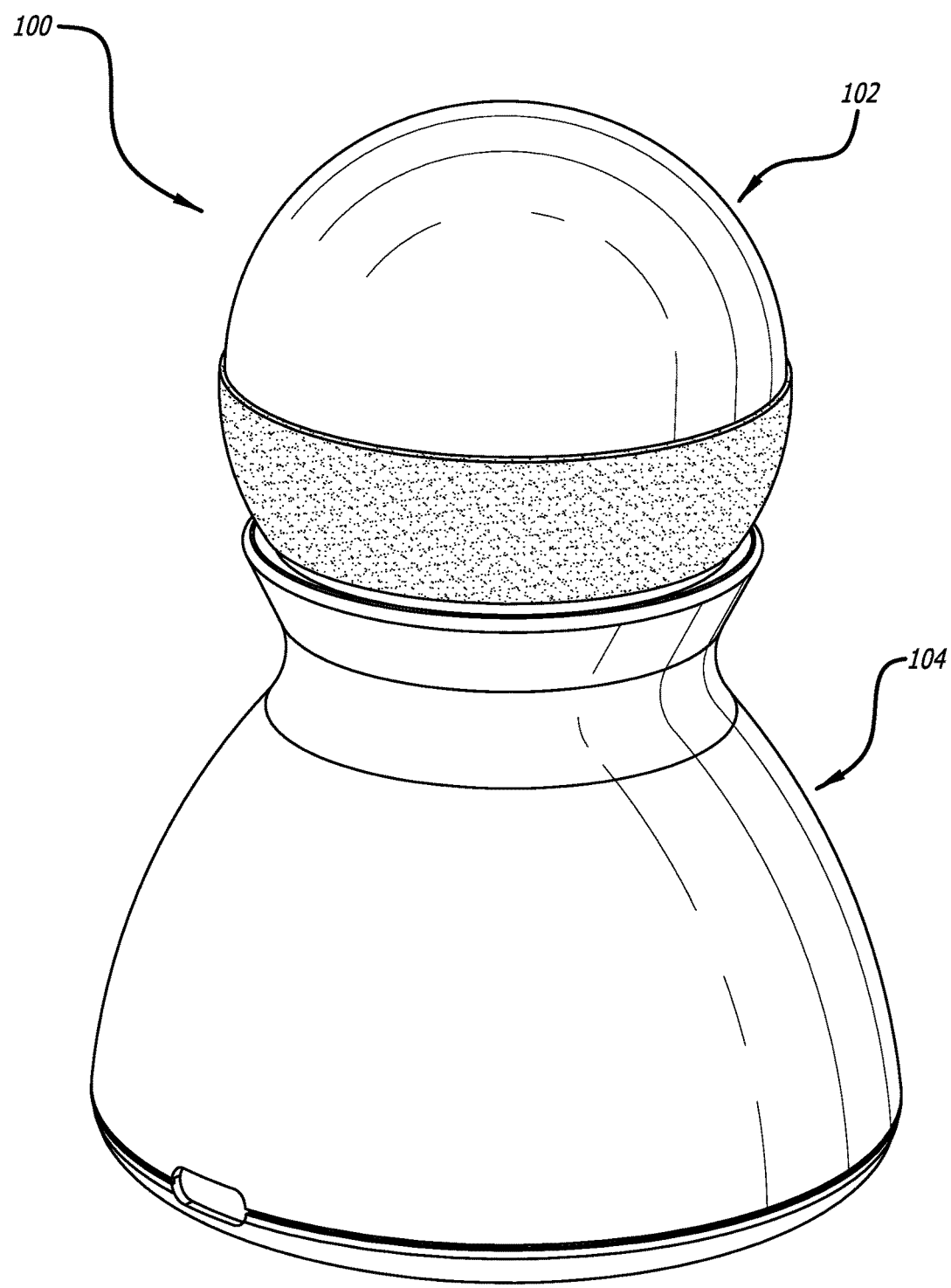
FIGS. 1A and 1B are perspective illustrations of a cardiac monitoring system that includes a portable device and a dock-top case for holding the device.
Figure 1B:
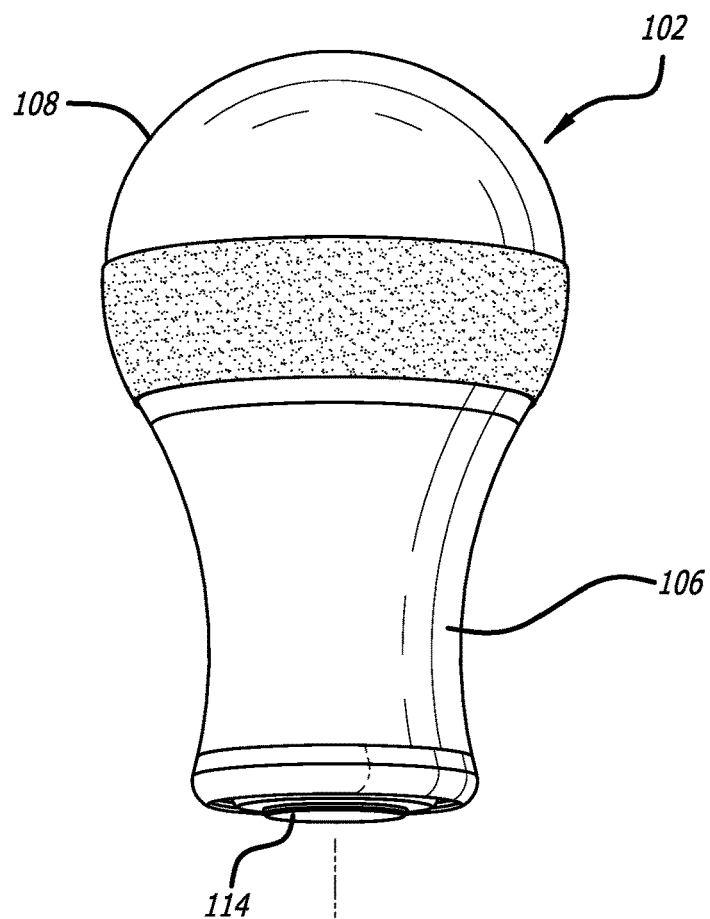
Figure 1B:
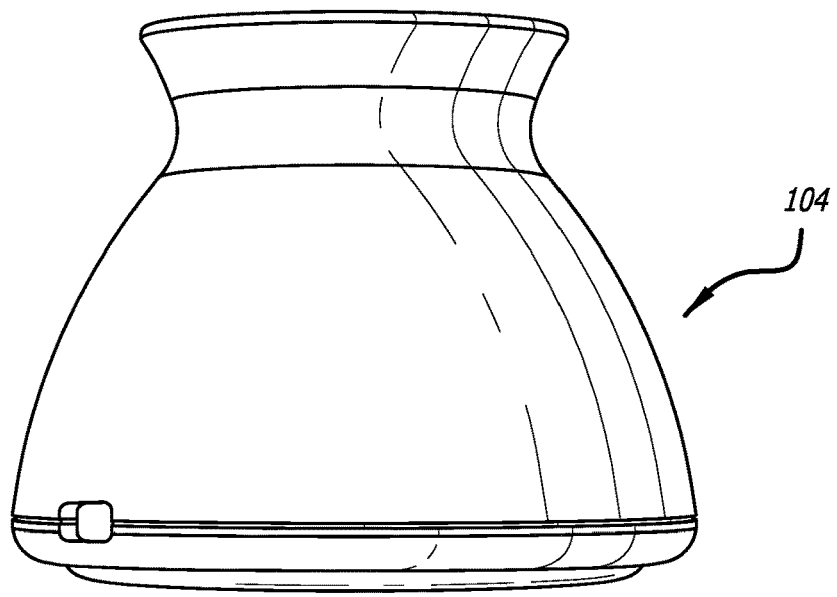

With reference to FIGS. 1A and 1B, a cardiac monitoring system 100 includes a portable device 102 and a dock-top case 104 for holding the device. As described further below, the portable device 102 and the dock-top case 104 include respective charging coils that enable charging of a power supply of the device.

Figure 2:
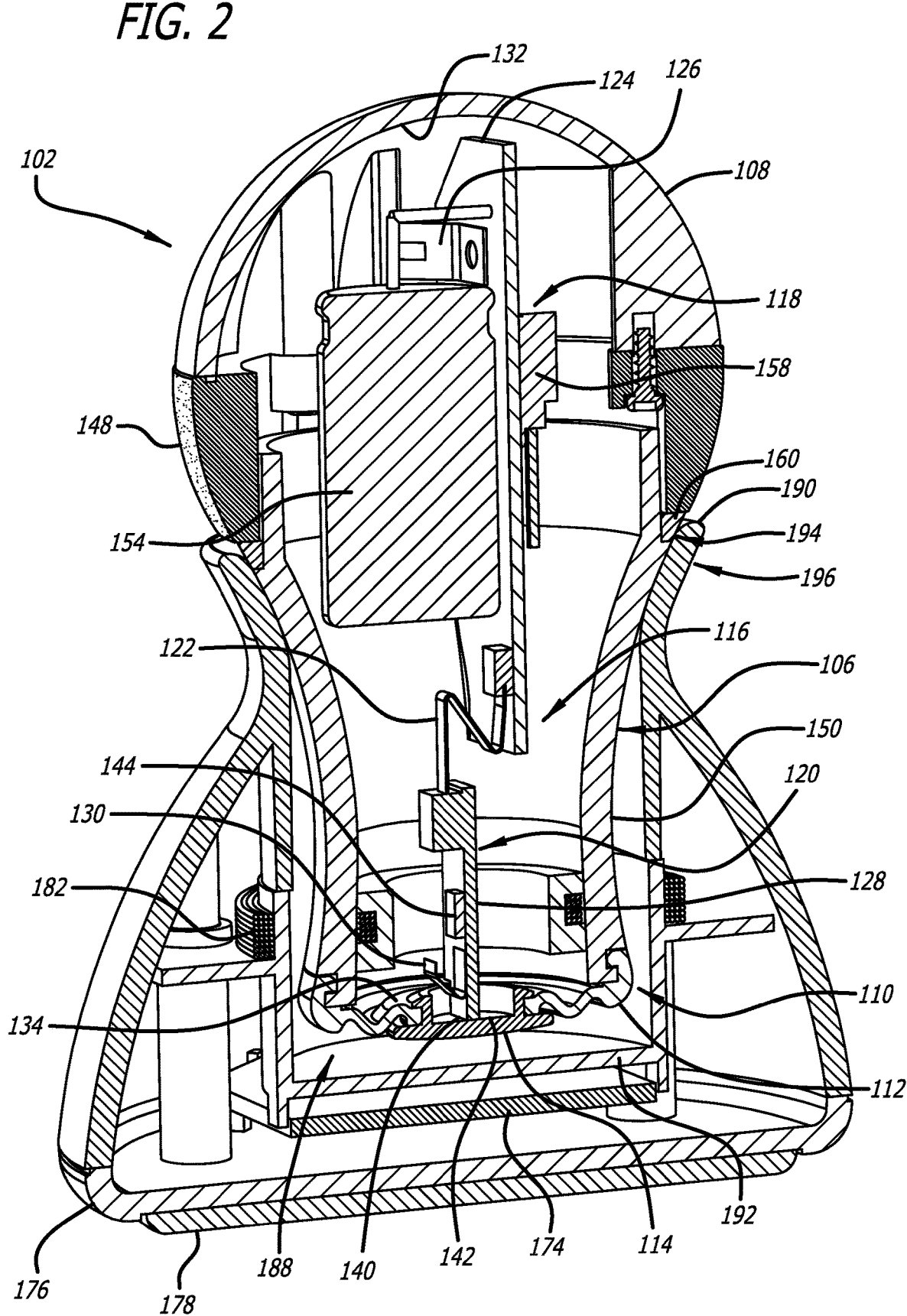
FIG. 2 is a perspective, cross-section illustration of the cardiac monitoring system with the portable device placed in the dock-top case.
Figure 3A:
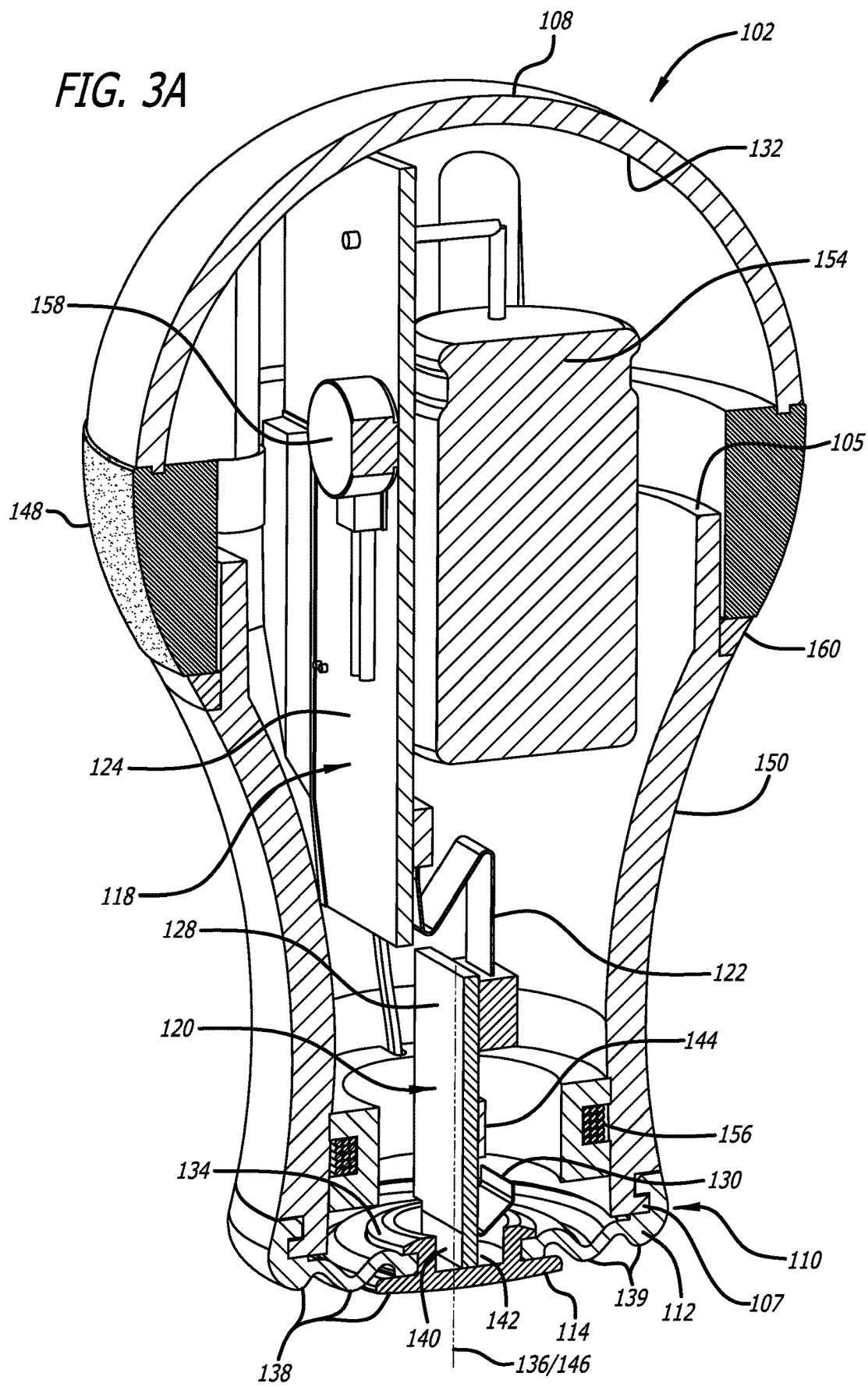
FIG. 3A is a perspective, cross-section illustration of the portable device.

With reference to FIGS. 2, 3A, 3B, 4A, 4B, and 6, the portable device 102 includes a main body 106, a first electrode 108, a suspension structure 110 with a second electrode 114, and an electronics assembly 116 contained within an enclosure formed by the first electrode, the main body, and the suspension structure. A textured ring 148 may be located between the first electrode 108 and a portion of the main body 106. The textured ring 148 provides enhanced gripping of the portable device 102. Referring to FIG. 3A, the main body 106 has a length, a first end 105, a second end 107, and an axis 136 along the length. In some embodiments, the main body has a tapered sidewall 150. An illumination ring 160 may surround all or a portion of the main body 106 and may be just beneath the textured ring 148. In one configuration, the illumination ring surrounds the entirety of the main body and is thus provides the ability for the user to see it at any angle while in use or in the dock-top case 104.

The first electrode 108 is associated with the first end 105 of the main body 106 and has a geometry that enables placement in the palm of a hand. In one configuration, the first electrode 108 has a non-planar hemispherical or dome shape. The first electrode 108 may be made of one or more metals, such as zinc, aluminum, magnesium, and/or nickel. The suspension structure 110 with the second electrode 114 is associated with the second end 107 of the main body 106 and is configured for displacement in a direction of the axis 136 of the main body. The second electrode 114 has a geometry that enables placement against a chest. In one configuration, the second electrode 114 has a planar disc shape. The second electrode 114 may be made of either carbon-filled plastic coated with Ag/AgCl or made of one or more metals, such as zinc, aluminum, magnesium, and/or nickel. The area of the exterior surface of the first electrode 108 is greater than the area of the exterior surface of the second electrode 114, and in some embodiments is between 10 and 20 times greater. For example, in one configuration, the area of the exterior surface of the first electrode 108 is 5.8 square inches, while the patient contact area of the second electrode 114 is 0.3 square inches, which is similar in size as traditional ECG electrodes. Other size surface areas are contemplated, and the device disclosed herein is in no way limited to these example sizes.

With reference to FIGS. 3A, 3B, 4A, and 4B, the suspension structure 110 includes a flexible isolation ring 112 defining an opening 113. The second electrode 114 is associated with the opening and is mechanically coupled to the flexible isolation ring 112. The flexible isolation ring 112 includes an undulating surface defined by concentric ribs 139 that forms a heart sound pickup when the second electrode 114 is pressed against the chest. The flexible isolation ring 112 is a solid circular body that helps stabilize the second electrode 114 against the chest and provides a means to rest the portable device 102 against the chest without impeding the function of the heart sound pickup. The thickness of the second electrode 114 combined with the tension in the flexible isolation ring 112 ensure that the heart sound pickup makes positive contact with the body tissue for coupling heart sound vibration to the motion sensor 144.

Figure 3B:
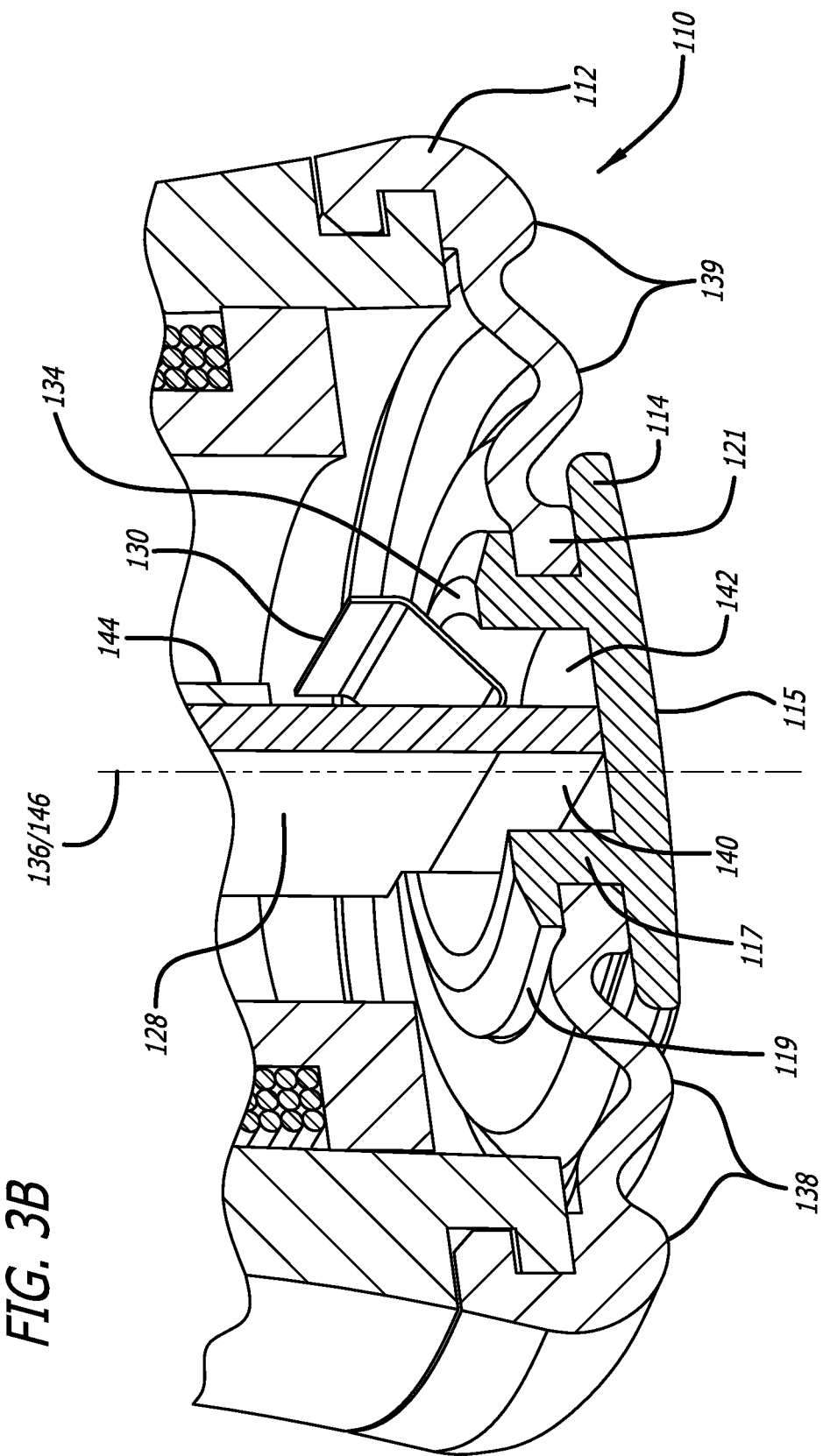
FIG. 3B is a perspective, cross-section illustration of a portion of the portable device.

Referring to FIG. 3B, regarding the mechanical coupling of the second electrode 114 and the flexible isolation ring 112, the second electrode 114 includes a bottom plate 115 and an annular wall 117 extending from the upper surface of the bottom plate. The annular wall 117 includes a rim 119 at the top that extends outward from the annular wall. The bottom of the rim 119, outer surface of the annular wall 117 and the upper surface of the bottom plate 115 define an annular groove of the second electrode 114. This annular groove is sized to receive a portion 121 of the flexible isolation ring 112 and provides a mechanism through which the second electrode 114 is mechanically coupled to the flexible isolation ring in a way that enables easy removal and replacement. The interior of the annular wall 117 exposes a portion of the upper surface 142 of the bottom plate 115 and it is this surface against which the distal end 140 of the second printed circuit board 128 abuts.

Figure 4A:
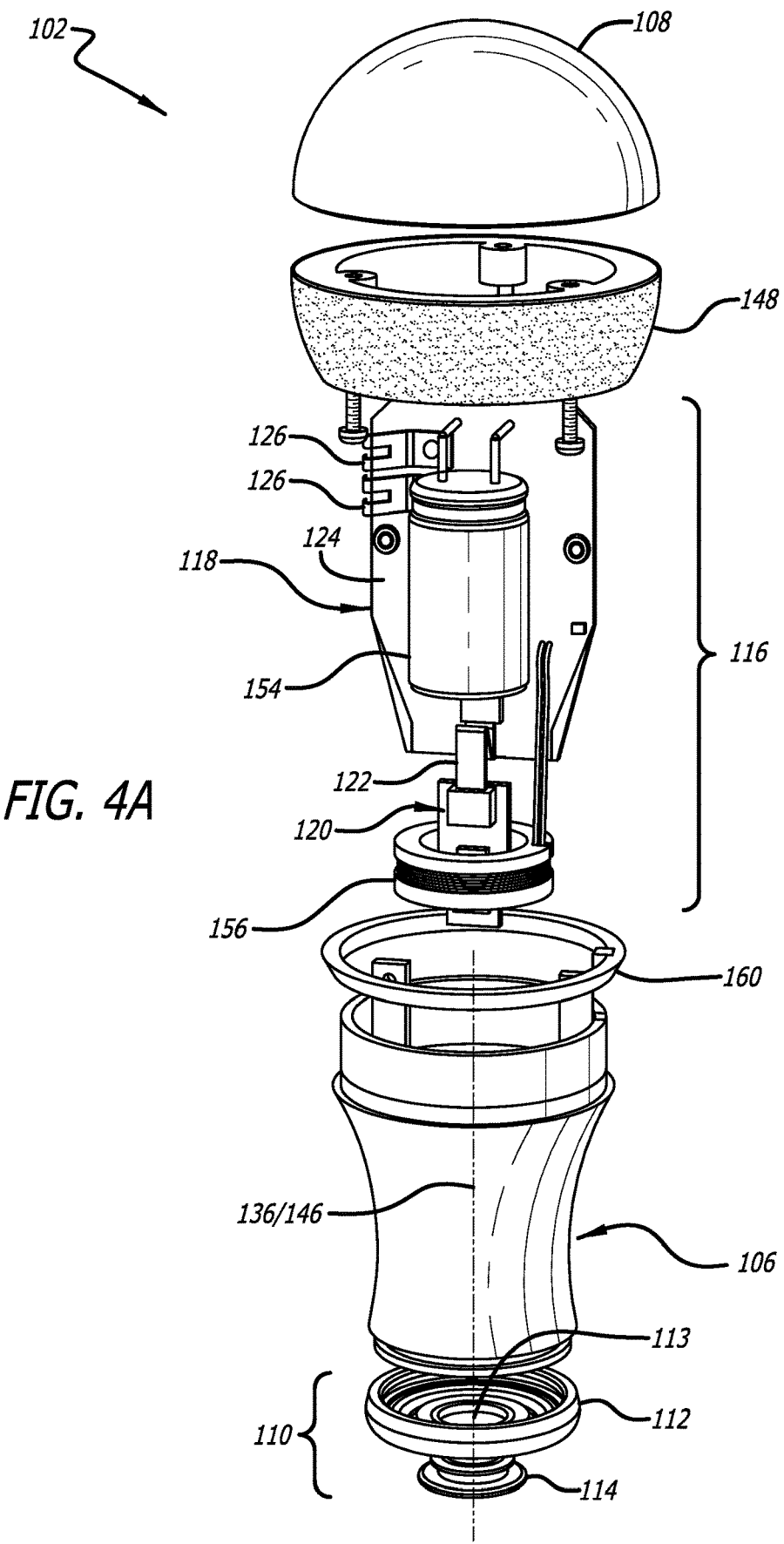
FIGS. 4A and 4B are exploded illustrations of the portable device from different perspectives.
Figure 4B:
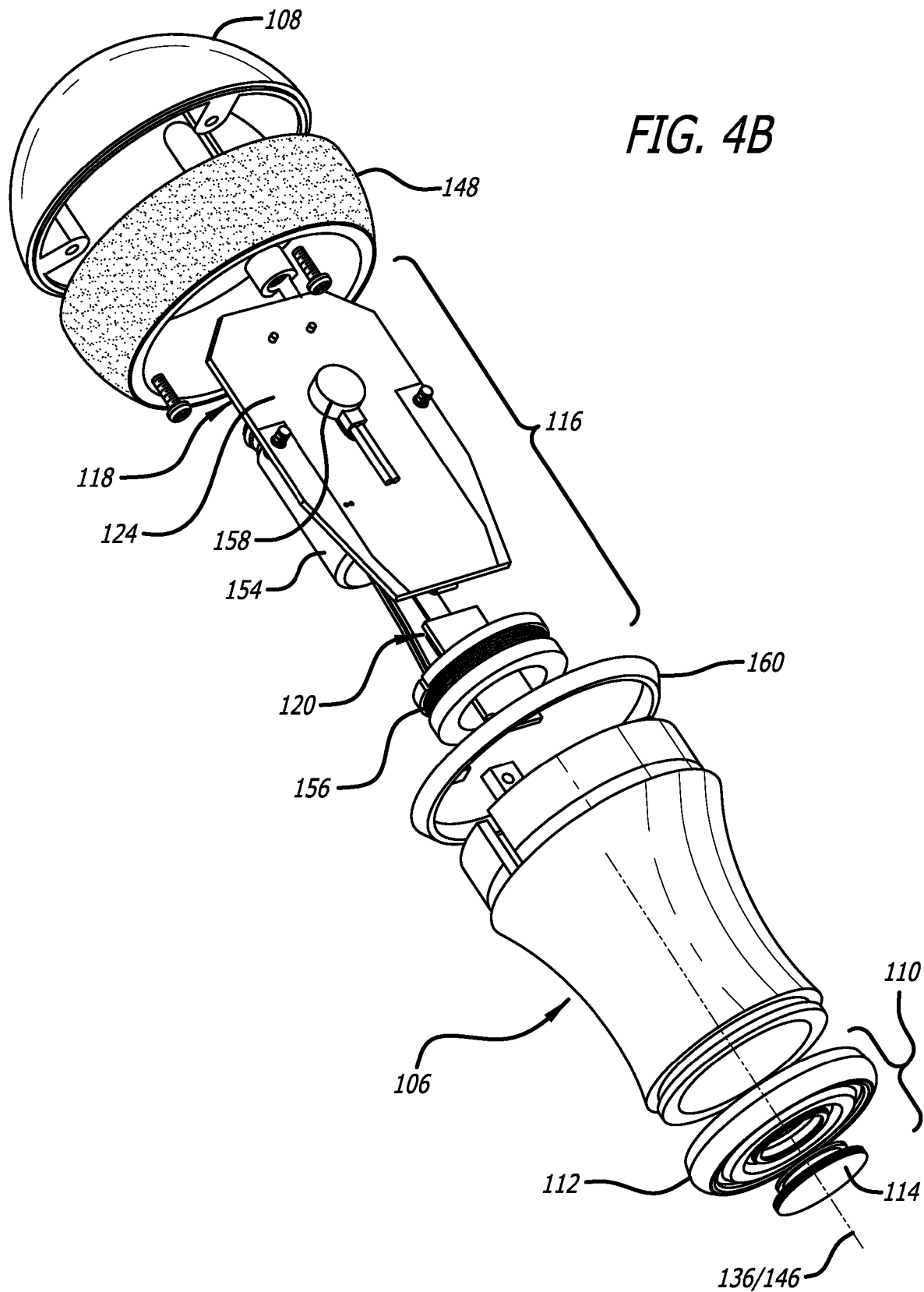

With reference to FIGS. 3A, 4A and 4B, the electronics assembly 116 includes a first subassembly 118, a second subassembly 120, and a flexible coupling 122 configured to electrically couple the first subassembly with the second subassembly. To this end, as shown in FIG. 3A, a first end of the flexible coupling 122 is electrically coupled to a coupling feature the first subassembly 118, while a second end of the flexible coupling is electrically coupled to coupling of the second subassembly 120. The flexible coupling 122 may have any one of a variety of configurations. For example, the flexible coupling 122 may be configured as a Z-bend flex wire structure, such as shown in FIGS. 3A, 4A and 4B. In other configurations, the flexible coupling may be a coiled wire structure.

The first subassembly 118 is electrically coupled to the first electrode 108 and secured relative to the main body 106 to prevent displacement of the first subassembly in a direction of the axis 136 of the main body. In some embodiments the second subassembly 120 is fixedly electrically coupled with the second electrode 114. In other embodiments, the second subassembly 120 is configured to electrically coupled with and decouple from the second electrode 114. As shown in FIG. 3A, the flexible coupling 122 is located between the first subassembly 118 and the second subassembly 120 and is configured to enable up/down displacement of the second subassembly relative to the first subassembly and in a direction of the axis 136 of the main body 106. The flexible coupling 122 is routed in a way to avoid introducing rubbing sounds that may interfere with the operation of the motion sensor 144.

Referring to FIGS. 2 and 4A, the first subassembly 118 of the electronics assembly 116 includes a first printed circuit board 124 and at least one first biasing mechanism 126. The first biasing mechanism 126 is electrically coupled to the first printed circuit board 124 and extends from the printed circuit board into abutting contact with an electrically conductive region 132 of the first electrode 108. The conductive region 132 may correspond to an interior surface of the first electrode 108. The first biasing mechanism 126 may be a spring contact positioned relative to the interior surface 132 of the first electrode 108 so that the spring contact presses against the interior surface to form an electrical connection with the first electrode 108. In some embodiments, the portable device 102 includes a pair of first biasing mechanism 126 for redundancy, each arranged to press against the interior surface 132 to form an electrical connection with the first electrode 108.

Figure 6:
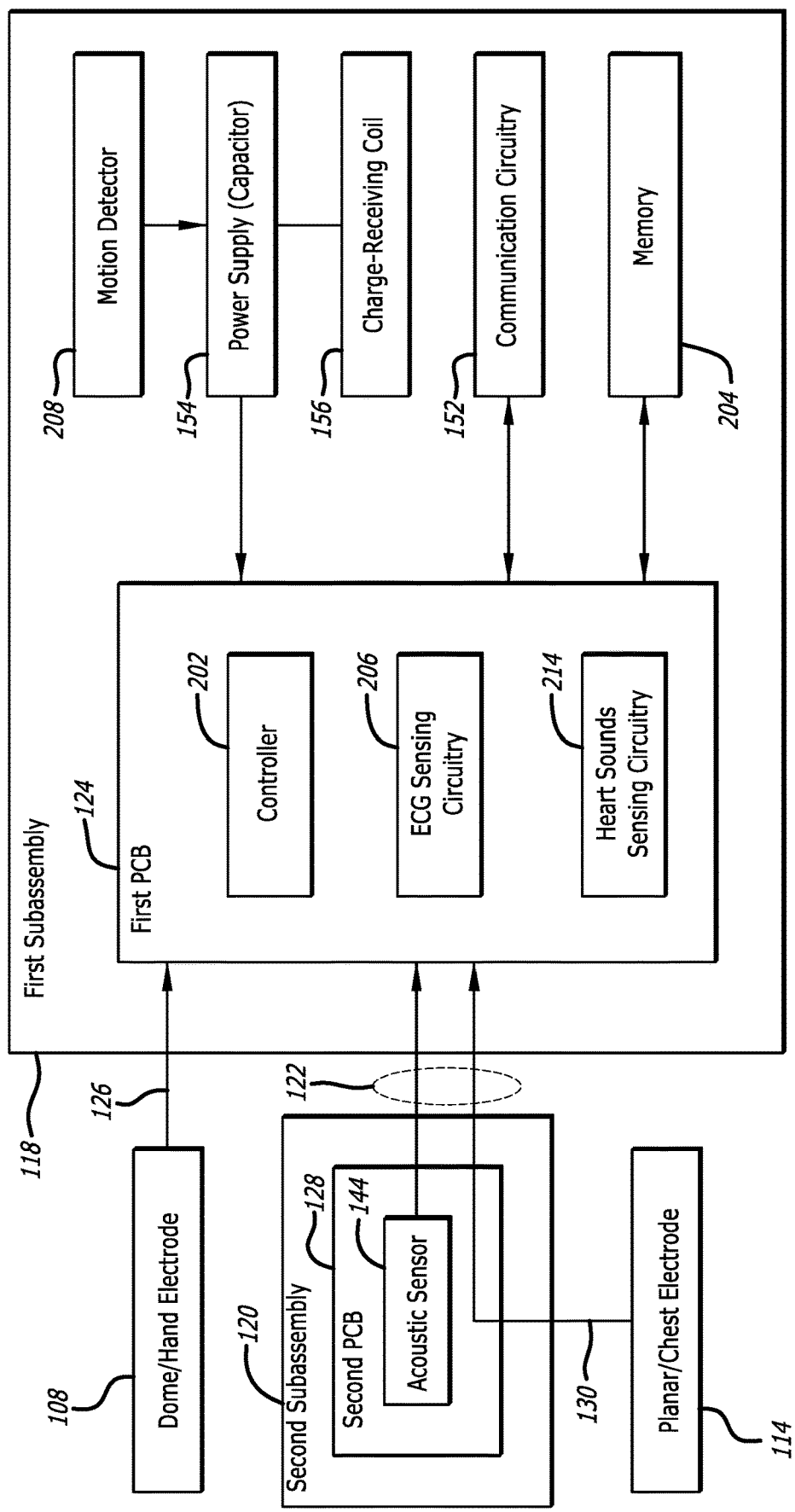
FIG. 6 is a schematic diagram of the portable device.

With reference to FIG. 6, in some embodiments the first subassembly 118 includes a controller 202, ECG sensing circuitry 206, heart sounds sensing circuitry 214, communication circuitry 152, a memory 204, a power supply 154, a charge-receiving coil 156, and a haptic transducer 158. The ECG sensing circuitry 206 is coupled to the first electrode 108 and the second electrode 114 and is configured in accordance with standard, known ECG sensing technology to detect electrical activity of the heart through a sensing vector defined by the electrodes and to provide signals representing such activity, including for example cardiac cycles including atrial and ventricular depolarizations and repolarizations. The heart sounds sensing circuitry 214 is coupled to the motion sensor 144 and is configured in accordance with standard, known heart sounds sensing technology to detect heart sounds through the acoustic sensor and to provide signals presenting heart sounds, including for example cardiac cycles including S1 through S4 heart sounds.

Continuing with reference to FIG. 6, the controller 202 is configured to receive the signals representing sensed ECG activity from the ECG sensing circuitry 206. In some embodiments, the controller 202 is further configured to create a communications data packet that includes the signals representing sensed ECG activity and to transmit the data packet through the communication circuitry 152. In some embodiments, the controller 202 is further configured to create a memory data packet that includes the signals representing sensed ECG activity and to store the data packet in memory 204 for later retrieval therefrom and transmission through the communication circuitry 152.

Likewise, the controller 202 is configured to receive the sensed heart sounds activity from the heart sounds sensing circuitry 214. In some embodiments, the controller 202 is further configured to create a communications data packet that includes the signals representing the sensed heart sounds activity and to transmit a communications data packet through the communication circuitry 152. In some embodiments, the controller 202 is further configured to create a memory data packet that includes the signals representing sensed heart sounds activity and to store the data packet in memory 204 for later retrieval therefrom and transmission through the communication circuitry 152.

The communication circuitry 152 includes a receiver/transmitter and antenna, and may be a Bluetooth Low Energy Radio or other wireless communications technology. The first subassembly 118 may also include a motion detector 208 that detects removal of the portable device 102 from the dock-top case 104 and activates the power supply 154 to thereby turn on the device. The power supply 154 may be a capacitor. The charge-receiving coil 156 is configured to receive charging energy from a charge-transmitting coil of the dock-top case 104.

Referring to FIGS. 2, 3A, and 3B, the second subassembly 120 of the electronics assembly 116 includes a second printed circuit board 128 and, in some embodiments, a second biasing mechanism 130. The second biasing mechanism 130 is electrically coupled to the second printed circuit board 128 and extends from the second printed circuit board to a location relative to an electrically conductive region 134 of the second electrode 114. The second biasing mechanism 130 is located relative to the electrically conductive region 134 of the second electrode 114 such that a displacement of the suspension structure 110 along the axis 136 of the main body 106 enables the second electrode 114 to transition between an engaged state and a disengaged state. In an engaged state, the second biasing mechanism 130 is electrically coupled with the electrically conductive region 134 of the second electrode 114. In a disengaged state, the second biasing mechanism 130 is electrically decoupled from the electrically conductive region 134 of the second electrode. In other embodiments, the second subassembly 120 does not include a second biasing mechanism 130 and electrical coupling between the second printed circuit board 128 and the second electrode 114 is provided by soldering the second printed circuit board to the second electrode.

With reference to FIG. 3B, the suspension structure 110 is configured to transition the second electrode 114 from the disengaged state to the engaged state responsive to an application of a sufficient force to an exterior surface 138 of the suspension structure 110. The force may be applied to one or more ribs 139 of the flexible isolation ring 112 and the bottom plate 115 of the second electrode 114. The force may result, for example, from the pressing of the bottom plate 115 of the second electrode 114 and the suspension structure 110 against the chest. Conversely, the suspension structure 110 is configured to the transition the second electrode 114 from the engaged state to the disengaged state responsive to a removal of the sufficient force from the bottom plate 115 of the second electrode 114 and the exterior surface 138 of the suspension structure. The removal of such force may result, for example, from the removing of the suspension structure 110 from the chest.

With reference to FIGS. 3A and 3B, the second printed circuit board 128 has a distal end 140 in abutting contact with an upper surface 142 of the second electrode 114. The second subassembly 120 of the electronics assembly 116 also includes a motion sensor 144 associated with the second printed circuit board 128. The motion sensor 144 may be, for example, a low-noise MEMS accelerometer. Displacement of the suspension structure 110 in the direction of the axis 136 of the main body 106 results in displacement of the second electrode 114 and corresponding displacement of the second printed circuit board 128 and the motion sensor 144. The second printed circuit board 128, the second electrode 114, and the flexible isolation ring 112 form a movable portion of the portable device 102 that has a center of mass in alignment or near alignment with a center line 146 extending through the center of the suspension structure 110 in a direction of the axis 136 of the main body 106. This movable portion may be referred to has a transducer system. Keeping the center of mass of the transducer system in alignment or near alignment with the center line 146 avoids rotational movement of the second printed circuit board 128 in response to vibration forces. The mass of the movable portion (e.g., the second printed circuit board 128, the second electrode 114, and the flexible isolation ring 112) combined with the elasticity of the body tissue against which the second electrode is pressed during use, form a low-pass filter limiting the usable signal bandwidth of the transducer system. By keeping the mass of the movable portion low, a desired bandwidth is accomplished.

Thus, disclosed herein is a portable device 102 that provides for far-field sensing of ECG activity through a vector formed by a first electrode site at the hand a second electrode site at the chest. In comparison to near-field vectors formed between two chest electrodes, the vector of the disclosed portable device 102 produces signals of ECG activity with less noise, and ones in which atrial events, e.g., p-waves, are more visible. The dome shape of the first electrode provides a large surface area that enables the capture of quality ECG activity without the need for gel and a shape that provides an ergonomic fit and grip with hand.

Figure 5:
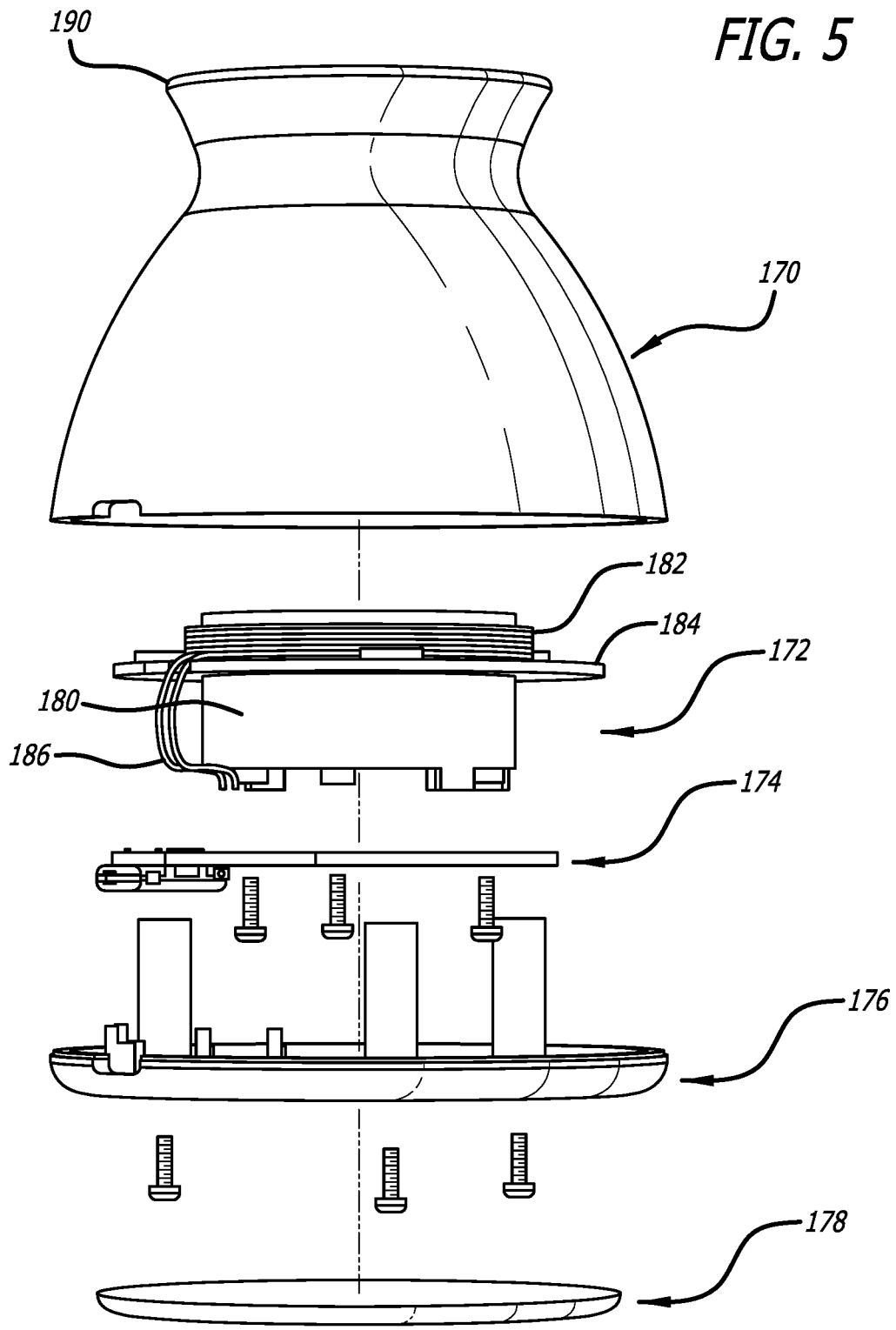
FIG. 5 is a perspective, exploded illustration of the dock-top case of FIGS. 1A and 1B.

With reference to FIGS. 2 and 5, the dock-top case 104 includes a housing 170, a charging coil assembly 172, a dock charging printed circuit board 174, a case bottom 176, and a rubber base pad 178. The charging coil assembly 172 includes a cylindrical structure 180 having an upper annular flange 184 that supports a charge-transmitting coil 182. The charge-transmitting coil 182 is electrically coupled to the dock charging printed circuit board 174 through conductors 186. As shown in FIG. 2, when assembled, the housing 170 and the cylindrical structure 180 of the charging coil assembly 172 from a cavity 188 configured to receive a docking portion of a portable device 102. Respective dimensions of the cavity 188 and a docking portion of a portable device 102 are such that the charge-transmitting coil 182 of the dock-top case 104 and the charge-receiving coil 156 of the portable device are vertically aligned to facilitate charging.

More specifically, the height of the cavity 188 from the top rim 190 of the dock-top case 104 to the bottom of the bottom 192 of the cylindrical structure 180, and the diameter of the opening at the top rim are sized relative to the height of the portable device 102 between the bottom of the second electrode 114 and the junction 194 of the tapered sidewall 150 and the illumination ring 160 and the diameter of the portable device 102 at the junction, such that when the portable device is placed in the cavity 188 of the dock-top case 104, the portion of the portable device at the junction 194 is in abutting contact with a tapered region 196 of the dock-top case, and the charge-receiving coil 156 of the portable device is vertically aligned with the charge-transmitting coil 182 of the dock-top case, and the bottom of the second electrode 114 of the portable device is suspended above the bottom 192 of the cylindrical structure 180.

Thus, disclosed herein a cardiac monitoring system 100 that includes a portable device 102 and dock-top case 104. The portable device 102 has a main body 106 with a charge-receiving coil 156. The dock-top case 104 includes a cavity 188 and a charge-transmitting coil 182 that surrounding the cavity. The cavity 188 is configured to receive a docking portion of the main body 106 of the portable device 102 such that the charge-receiving coil 156 of the portable device aligns with the charge-transmitting coil 182 of the case.

Figure 7:
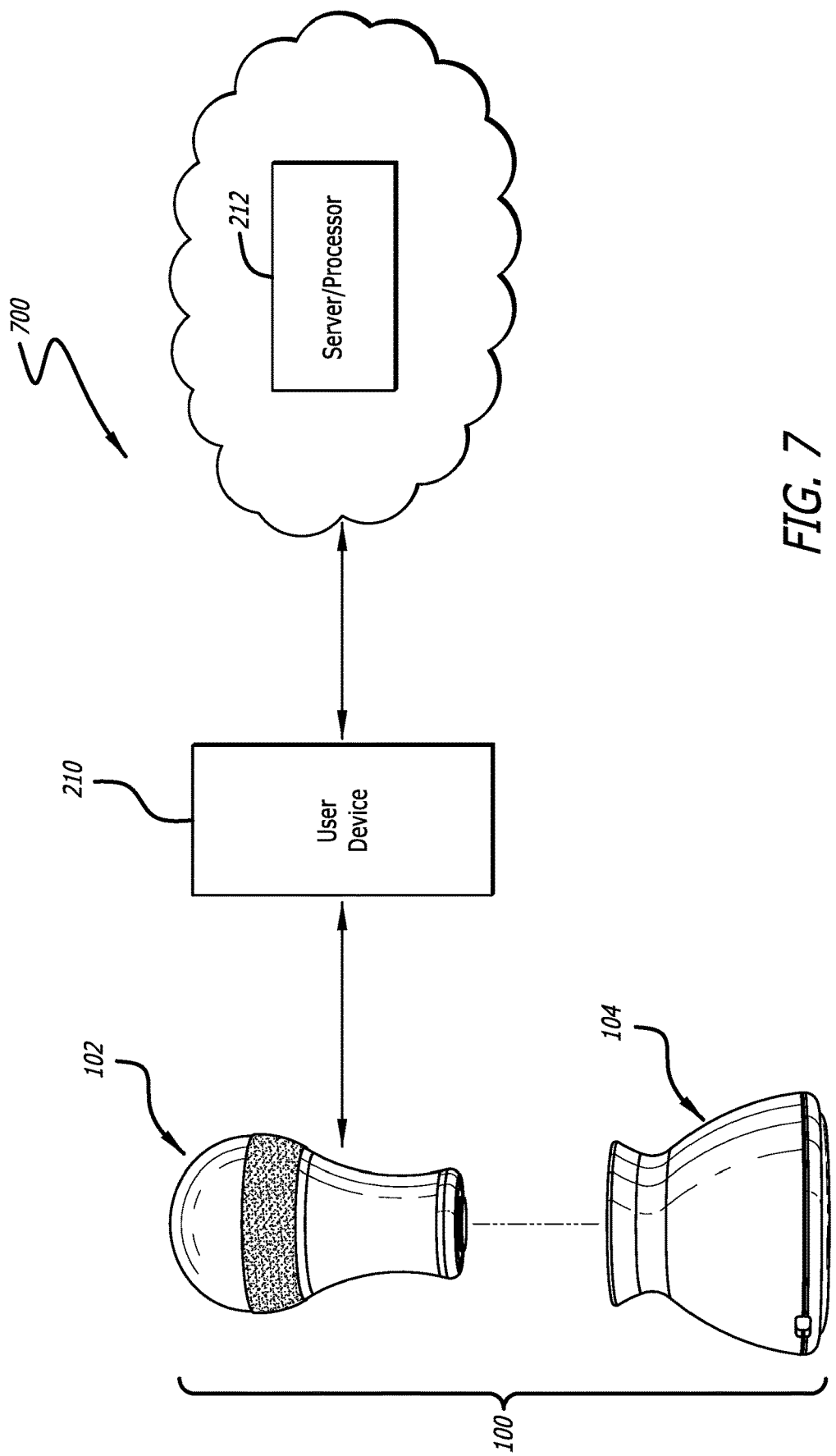
FIG. 7 is a block diagram of a cardiac monitoring network including a cardiac monitoring system, a user device, and a cloud based server/processor.

FIG. 7 is a block diagram of a cardiac monitoring network 700 that includes a cardiac monitoring system 100, a user device 210, and a cloud based server/processor 212. The cardiac monitoring system 100 includes a portable device 102 and a dock-top case 104. An example application of the cardiac monitoring system 100 is described below with reference to FIG. 8.

Figure 8:
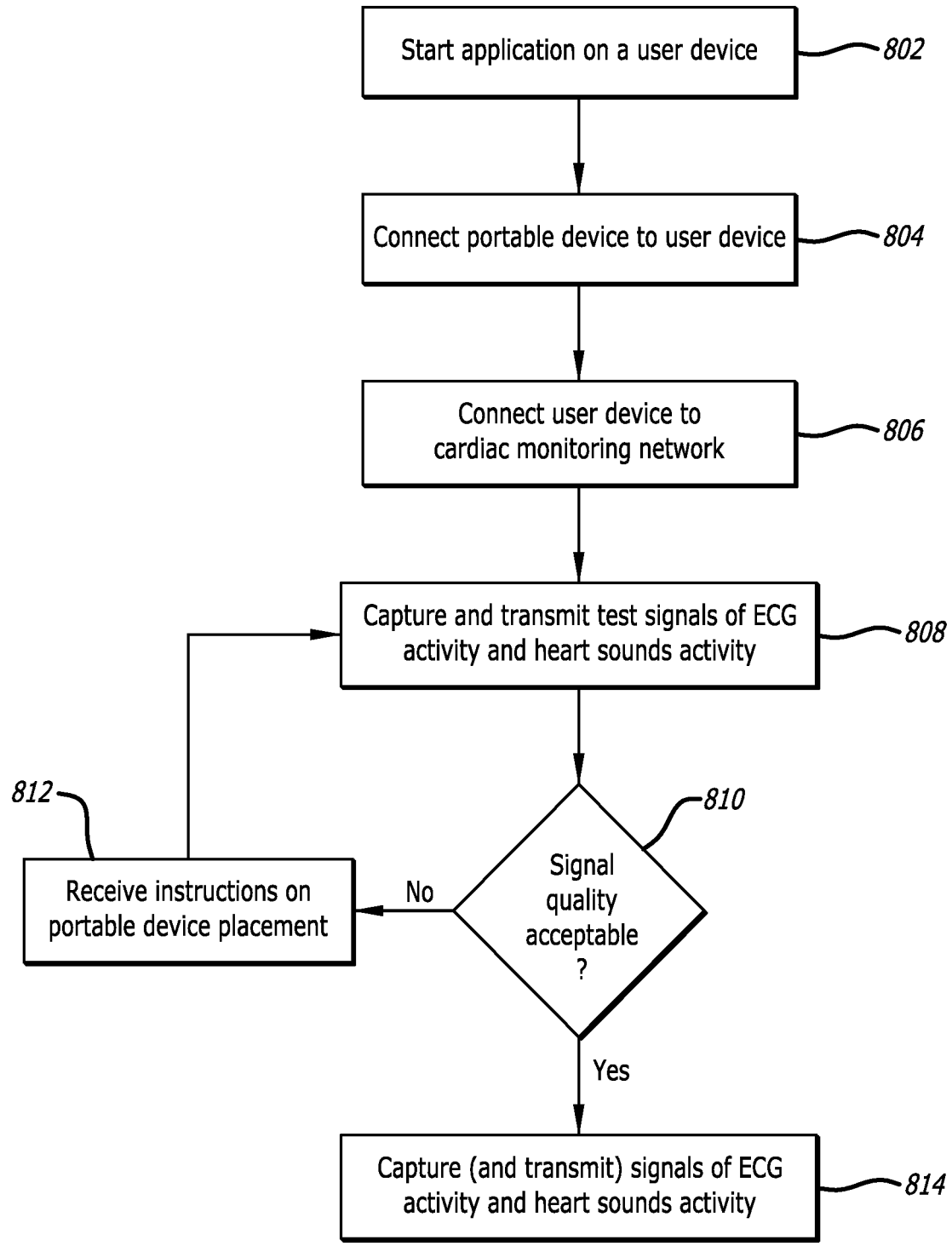
FIG. 8 is a flowchart of use of the cardiac monitoring network of FIG. 7.

With reference to FIG. 8, an example application of the cardiac monitoring system of FIGS. 1-6 within a cardiac monitoring network 700 is now described.

At block 802, an application is started on a user device 210. The user device 210 may be a phone, tablet, laptop, or desktop computer.

At block 804, a portable device 102 is connected to the user device 210. To this end, a user may remove the portable device 102 from the dock-top case 104. Upon removal from the dock-top case 104, the portable device 102 automatically turns on and connects to the user device 210 via the communication circuitry 152.

At block 806, the user device 210 is connected to a server/processor 212 of the cardiac monitoring network 700. The connection between the user device 210 and the server/processor 212 may be made using standard communication technologies, including for example, wireless cellular technology or wired Internet technology.

At block 808, test signals corresponding to sensed ECG activity and sensed heart sounds activity are captured. To this end, and with particular reference to FIGS. 9A and 9B, the portable device 102 is held with the right hand and pressed lightly against the chest in the V3 or V4 precordial lead location for approximately 10 seconds. During this time, the portable device 102 captures separate ECG activity and heart sounds activity signals and transmits each of these signals to the user device 210 in real-time. The user device 210, in turn, transmits the respective ECG activity and heart sounds activity signals to the server/processor 212 of the cardiac monitoring network 700 in real-time.

At block 810, a determination is made regarding proper locating of the second electrode 114 on the chest and the quality of the ECG activity signal and the heart sounds activity signal. In some embodiments, the server/processor 212 may analyze each of the ECG test signal and the heart sounds test signal to determine if the electrodes 108, 114 and the suspension structure 110 of the portable device 102 are being held in positions that establish a proper ECG sensing vector and/or a proper audible capture of heart sounds. This is accomplished by comparing morphologic characteristics of the test signals to "fingerprint" signals previously captured during setup and patient training.

If it is determined that the quality of one or more of the test signal of ECG activity and the test signal of heart sounds activity is not acceptable, then the process proceeds to block 812 where instructions are received at the user device 210 from the server/processor 212 to the user device 210 regarding the positions of the electrodes 108, 114 and repositioning of the portable device 102. For example, one or more of an audible, visual, or tactile (haptic) feedback may be provided to the user, prompting them to adjust the position of the suspension structure 110 relative to the chest, and with it the location of the second electrode 114. Audible and visual feedback may be provided through the user device 210. Visual feedback may be provided by the illumination ring 160 of the portable device. Tactile feedback may be provided by a vibration mechanism or haptic transducer 158 of the portable device 102. The process then returns to block 808 where another set of test signals of ECG activity and heart sounds activity are captured after the position of the suspension structure 110 and the second electrode 114 are adjusted.

Returning to block 810, if it is determined that the quality of each of the ECG signal and the heart sounds signal is acceptable, then the process proceeds to block 814 where analysis signals of ECG activity and heart sounds activity are captured. To this end, the portable device 102 is maintained at its current position and continues to be held with the right hand and pressed lightly against the chest in the V3 or V4 precordial lead location for a minute or so. During this time, the portable device 102 captures signals of ECG activity and heart sounds activity and transmits them to the user device 210 in real-time. Alternatively, the signals of ECG activity and heart sounds activity may be stored in the memory 204 of the portable device 102 for subsequent transmission to the user device 210.

In some embodiments, upon receipt of the analysis signals of ECG activity and heart sounds activity, the user device 210 transmits the signals to the server/processor 212 of the cardiac monitoring network 700 in real-time. Alternatively, the signals of ECG activity and heart sounds activity may be stored in a memory of the user device 210 for subsequent transmission to the server/processor 212 of the cardiac monitoring network 700. In either case, upon receipt of qualified signals of ECG activity and heart sounds activity, the server/processor 212 analyzes the signals and transmits result to the user device 210.

Continuing with block 814, after capture and transmission of the analysis signals of ECG activity and heart sounds activity, the portable device 102 may be placed in the dock-top case 104 for storage and recharging.

Thus, disclosed herein is a cardiac monitoring network 700 that includes a portable monitoring device 102, a user device 210, and a network server 212. The portable device 102 has a first electrode 108 shaped to be placed in abutting contact with a palm of a user hand, and a second electrode 114 shaped to be placed in abutting contact with a chest of the user while the first electrode in abutting contact with a palm of a user hand. The portable device 102 also includes circuitry coupled to the first electrode 108 and the second electrode 114 that is configured to sense electrocardiogram (ECG) activity and communication circuitry 152 configured to transmit a signal of the sensed ECG activity. The user device 210 has communication circuitry configured to receive the signal of the sensed ECG activity from the portable device 102. The network server 212 has a communication interface configured to communicate with the user device 210 to receive the signal of the sensed ECG activity from the user device.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A device comprising:
    a main body having a length, a first end, a second end, and an axis along the length;
    a first electrode associated with the first end of the main body;
    a suspension structure associated with the second end of the main body, the suspension structure configured for displacement in a direction of the axis of the main body, the suspension structure including:
       a flexible isolation ring defining an opening, and
       a second electrode associated with the opening and mechanically coupled to the flexible isolation ring; and
    an electronics assembly comprising:
       a first subassembly electrically coupled to the first electrode and secured relative to the main body to prevent displacement of the first subassembly in a direction of the axis of the main body,
       a second subassembly arranged to electrically couple with the second electrode, and
       a flexible coupling between the first subassembly and the second subassembly configured to enable displacement of the second subassembly relative to the first subassembly and in a direction of the axis of the main body.

2. The device of claim 1, wherein the first subassembly comprises:
    a first printed circuit board; and
    a first biasing mechanism electrically coupled to the first printed circuit board and extending from the first printed circuit board into abutting contact with an electrically conductive region of an interior surface of the first electrode.

3. The device of claim 1, wherein the second subassembly comprises:
    a second printed circuit board; and
    a second biasing mechanism electrically coupled to the second printed circuit board and extending from the second printed circuit board to a location relative to an electrically conductive region of the second electrode.

4. The device of claim 3, wherein the second printed circuit board has a distal end in abutting contact with an inner surface of the second electrode, and the second subassembly further comprises:
    a motion sensor associated with the second printed circuit board;
    wherein displacement of the suspension structure in the direction of the axis of the main body comprises displacement of the second electrode and corresponding displacement of the second printed circuit board and the motion sensor.

5. The device of claim 4, wherein the second printed circuit board has a center of mass aligned with a center line extending through the center of the suspension structure in a direction of the axis of the main body.

6. The device of claim 1, wherein the flexible coupling of the electronics assembly is configured to electrically couple the first subassembly with the second subassembly.

7. The device of claim 6, wherein the flexible coupling comprises one of a coiled wire structure or a Z-bend flex wire structure.

8. The device of claim 1, wherein the first electrode has an exterior surface area in a range of 10 to 20 times greater than an exterior surface area of the second electrode.

9. The device of claim 1, wherein the first electrode is characterized by a non-planar geometric shape.

10. The device of claim 9, wherein the non-planar geometric shape is a dome.

11. The device of claim 1, wherein the second electrode is planar.

12. The device of claim 1, further comprising a textured ring between the first electrode and a portion of the main body.

13. The device of claim 1, wherein the main body has a tapered sidewall.

* * * * *